United States Patent [19]

Marciel

[11] Patent Number: Plant 7,548

[45] Date of Patent: Jun. 11, 1991

[54] ROSE PLANT NAMED DEVICIO

[75] Inventor: Stanley G. Marciel, Aptos, Calif.

[73] Assignee: DeVor Nurseries, Inc., Watsonville, Calif.

[21] Appl. No.: 456,849

[22] Filed: Dec. 18, 1989

[51] Int. Cl.[5] ..... A01H 5/00

[52] U.S. Cl. ..... Plt./20

[58] Field of Search ..... Plt. 20, 21, 28, 29

*Primary Examiner*—Howard J. Locker

*Attorney, Agent, or Firm*—Charles W. Rummler

[57] ABSTRACT

A new and distinct variety of rose plant distinguished by its continuous and profuse production under greenhouse conditions of relatively large flowers borne singly on strong upright stems having a length of about 65 to 80 cm. from the last flower cut, the plant itself being a vigorous, upright, free branching bush with abundant foliage and a total height from the ground of about 120 cm.

1 Drawing Sheet

BACKGROUND OF THE NEW PLANT

This new rose variety originated as a seedling of a hybrid produced by me at Pleasanton, Calif. by my crossing the variety Love Affair (U.S. Plant Pat. No. 3,287) with the variety Paul's Pink (U.S. Plant Pat. No. 4,613) as the pollen parent with the object of producing a new red flowering tea rose adapted for cut flower production. This particular seedling was selected for propagation because of its profuse production of relatively large blossoms carried on strong upright stems of a plant having a height of about 36 inches with abundant foliage and I propagated this plant by budding at Pleasanton, Calif. with excellent results. This kind of propagation was carried on through several successive generations which thereby conclusively determined that the novel characteristics of the parent plant would hold true from generation to generation and appear to be firmly fixed.

DESCRIPTION OF THE DRAWING

My new rose plant is illustrated by the accompanying photographic drawing which shows in full color a face view of a blossom in full bloom, the color rendition being as close to that specified herein as is reasonably possible to obtain by professional photographic procedures.

DESCRIPTION OF THE NEW VARIETY

The following is a detailed description of my new rose plant based upon observation of plants grown in greenhouse at Watsonville, Calif., with the color designations being according to The R.H.S. Colour Chart published by The Royal Horticultural Society of London, England.

THE PLANT

Origin: Seedling.

Parentage:

*Seed parent.*—Love Affair (U.S. Plant Pat. No. 3,287).

*Pollen parent.*—Paul's Pink (U.S. Plant Pat. No. 4,613).

Classification:

*Botanic.*—Hybrid tea rose.

*Commercial.*—Greenhouse Rose.

Form: Upright free branching bush.

Growth: Vigorous.

Height: About 120 to 125 cm.

Main stem length: About 90 cm. from last flower cut.

Flowering stem length: About 70 cm.

Foliage:

*Quantity.*—Abundant.

*Number of leaves.*—5 or 6, From last flower cut.

*Shape of leaf.*—Odd pinnate.

*Size.*—About 13 cm. long and about 10 cm. wide.

*Leaflets.*—Number: 5 or 7. Size: Average about 64 mm. long and about 47 mm. wide. Shape: Oval with serrated margins. Texture: Leathery. Aspect: Smooth and semi-glossy. Color: Upper side — Green 147-A. Under side — Green 147-B. Stipules: Hairy adnate. Petiolule: 1 mm. long. Rachis: About 53 mm. long with 5 leaflets. Character: Smooth with small spines. Ribs and veins: Depressed on upper side of leaf and slightly rounded on the lower side.

Thorns:

*Number.*—Few.

*Size.*—About 7 to 8 mm. long.

*Color.*—Green 145-B with greyed red 182-C at the tips.

THE BUD

Form: Slender and tapering and slightly pointed.

Size: About 37 mm. long and about 25 mm. wide.

Rate of opening: Slow.

Color of petals:

*When sepals first divide and when petals begin to unfurl.*—Spiraea Red 63-B.

Sepals:

*Number.*—Five.

*Shape.*—Branching.

*Character.*—Hooded over the bud. When the flower opens, the sepals curl back.

*Color.*—Inside — Green 138-D with 138-B at the tips and with white hairs. Outside — Green 143-B.

Calyx:

*Shape.*—Funnel-shaped.

*Size.*—Medium and broad.

*Splitting.*—Calyx does not split.

*Aspect.*—Smooth.

Flower stem:

*Length.*—About 70 cm.
*Character.*—Slender and erect.
*Color.*—Green 146-C.

THE FLOWER

Blooming habit: Continuous and profusely the year round, blooming freely under glass.
Size of bloom: Relatively large.
*Diameter.*—9 or 10 cm.
Borne: Singly.
Shape: High center when opening and tending to flatten as the bloom matures.
Petalage:
*Number.*—24.
*Arrangement.*—Imbricated.
*Form.*—Generally oval with ruffled margin and slightly notched apex.
*Texture.*—Soft.
*Aspect.*—Velvety.
*Color.*—Outer petal body — Tyrian Purple 61-C. Base — Chartruese 154-C. Reverse side body — Rose Bengal 61-D. Base — Chartruese 154-C. Inside petals and petaloids — Rose Bengal 57-B. Base — Naples Yellow 11-C. Reverse side — Rose Bengal 61-C.
Petaloids:
*Number.*—5 to 8.
*Size.*—About 13 mm. long.
*Color.*—Rose Bengal 57-B with Napels Yellow 11-C base.
Discoloration after full bloom: Slight.
Persistence: The flowers hang on and dry.
Fragrance: Like that of fresh raspberries.

Disease resistance: Moderately resistant to mildew, rust, and black spots as observed at Pleasanton, Calif.
Lasting quality: Long-lasting on the plant and moderate as a cut flower.

THE REPRODUCTIVE ORGANS

Stamens:
*Number.*—98.
*Arrangement.*—Introse.
*Anthers.*—Size: About 4 mm. Color: Yellow Orange 22-A.
*Filaments.*—Length: About 9 mm. Color: Red 36-D.
*Pollen.*—Color: Yellow Orange 22-A.
Pistils:
*Number.*—73.
*Styles.*—Length: About 12 mm. Color: Yellow 8-D.
*Stigmas.*—Color: Tipped with Red 38-B.
Character of the ovaries: Long, slender, slightly flattened and covered with silvery hairs.

THE FRUIT

Fertility: The fruit is fertile.
Shape: Oblong, pear-shaped.
Color: Greyed Orange 167-B.

I claim:

1. The new and distinct variety of greenhouse rose plant substantially as herein shown and described, characterized in particular by its continuous and profuse production of relatively large flowers having Tyrian Purple outer petals and Rose Bengal colored inside petals and florets, the plant itself having a free branching growth habit and abundant production of foliage.

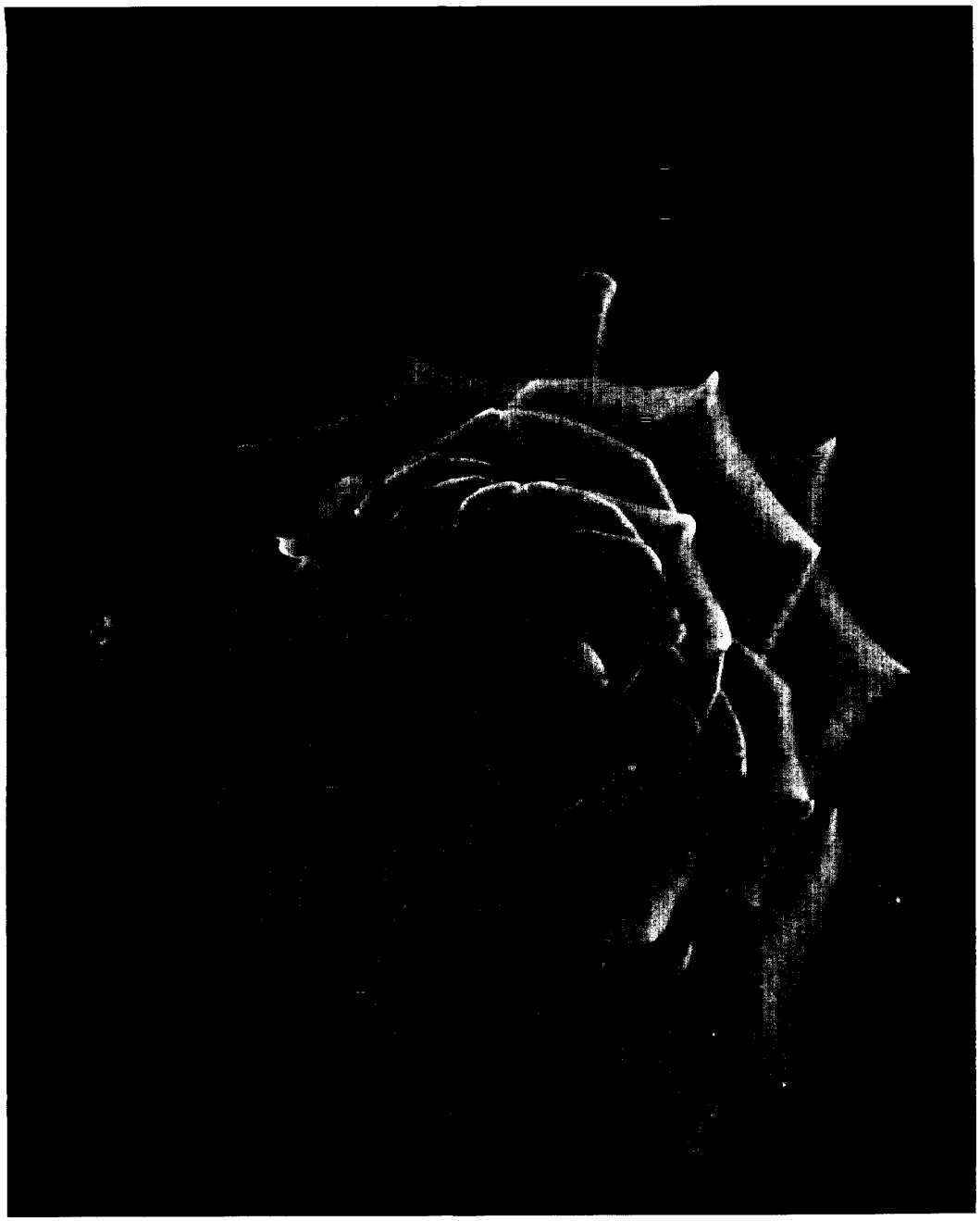

* * * * *